US011596454B2

(12) United States Patent
Wall et al.

(10) Patent No.: US 11,596,454 B2
(45) Date of Patent: *Mar. 7, 2023

(54) SPINAL IMPLANT SYSTEM AND METHOD

(71) Applicant: WARSAW ORTHOPEDIC, INC., Warsaw, IN (US)

(72) Inventors: Daniel Paxton Wall, Cordova, TN (US); Adam Glaser, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 284 days.

This patent is subject to a terminal disclaimer.

(21) Appl. No.: 16/538,247

(22) Filed: Aug. 12, 2019

(65) Prior Publication Data

US 2019/0357948 A1 Nov. 28, 2019

Related U.S. Application Data

(63) Continuation of application No. 15/661,962, filed on Jul. 27, 2017, now Pat. No. 10,463,404.

(51) Int. Cl.
*A61B 17/70* (2006.01)
*A61B 34/20* (2016.01)
(Continued)

(52) U.S. Cl.
CPC .......... *A61B 17/7082* (2013.01); *A61B 17/86* (2013.01); *A61B 17/8886* (2013.01); *A61B 34/20* (2016.02); *A61B 90/39* (2016.02)

(58) Field of Classification Search
CPC ... A61B 17/7082; A61B 17/86; A61B 17/861; A61B 17/8615; A61B 17/862; A61B 17/8886
(Continued)

(56) References Cited

U.S. PATENT DOCUMENTS 2,691,979 A 10/1954 Watson
5,390,383 A 2/1995 Carn
(Continued)

FOREIGN PATENT DOCUMENTS

CN 1092637 A 9/1994
CN 101856263 A 10/2010
(Continued)

OTHER PUBLICATIONS

European Patent Office, 80298 Munich, Germany, European Search Report, European Patent Application 18 837 456.5 dated Mar. 25, 2021.
(Continued)

*Primary Examiner* — Eduardo C Robert
*Assistant Examiner* — David C Comstock
(74) *Attorney, Agent, or Firm* — Sorell, Lenna & Schmidt, LLP

(57) ABSTRACT

A surgical instrument comprises a first member including a drive engageable with a first mating surface of a bone fastener. A second member is rotatable relative to the first member and includes an element engageable with a second mating surface of the bone fastener. An actuator is connected with the second member and includes visual indicia of engagement of the element with the second mating surface. Systems, spinal implants and methods are disclosed.

20 Claims, 11 Drawing Sheets

(51) Int. Cl.
*A61B 90/00* (2016.01)
*A61B 17/86* (2006.01)
*A61B 17/88* (2006.01)

(58) Field of Classification Search
USPC .......... 606/86 A, 97, 99, 102, 305, 308, 323
See application file for complete search history.

(56) References Cited

U.S. PATENT DOCUMENTS

| | | | |
|---|---|---|---|
| 5,885,299 A * | 3/1999 | Winslow | A61F 2/4601 |
| | | | 606/99 |
| 6,348,058 B1 * | 2/2002 | Melkent | A61B 17/1757 |
| | | | 600/429 |
| 6,752,832 B2 * | 6/2004 | Neumann | A61F 2/44 |
| | | | 623/17.15 |
| 7,189,214 B1 | 3/2007 | Saunders | |
| 7,234,180 B2 | 6/2007 | Horton et al. | |
| 7,290,302 B2 | 11/2007 | Sharps | |
| 7,496,980 B2 | 3/2009 | Sharps | |
| 8,277,510 B2 * | 10/2012 | Kleiner | A61F 2/447 |
| | | | 623/17.16 |
| 9,597,135 B1 | 3/2017 | Miller et al. | |
| 2004/0010261 A1 * | 1/2004 | Hoag | A61F 2/4607 |
| | | | 606/99 |
| 2007/0016219 A1 * | 1/2007 | Levine | A61B 90/39 |
| | | | 606/99 |
| 2008/0134434 A1 | 6/2008 | Celauro | |
| 2009/0005787 A1 | 1/2009 | Crall et al. | |
| 2009/0112220 A1 * | 4/2009 | Kraus | A61F 2/4455 |
| | | | 606/99 |
| 2010/0037397 A1 | 2/2010 | Wood | |
| 2010/0331897 A1 * | 12/2010 | Lindner | A61B 17/7044 |
| | | | 606/305 |
| 2011/0046683 A1 * | 2/2011 | Biedermann | A61B 17/7037 |
| | | | 606/305 |
| 2011/0313476 A1 | 12/2011 | McLean | |
| 2012/0123431 A1 | 5/2012 | Robinson | |
| 2012/0144689 A1 | 6/2012 | Skripps et al. | |
| 2013/0111666 A1 | 5/2013 | Jackson | |
| 2013/0282019 A1 | 10/2013 | Bouliane | |
| 2014/0109316 A1 | 4/2014 | Jackson et al. | |
| 2015/0250512 A1 | 9/2015 | Poker et al. | |
| 2016/0047394 A1 | 2/2016 | Lee et al. | |
| 2016/0302835 A1 | 10/2016 | Jackson | |
| 2017/0049651 A1 | 2/2017 | Lim et al. | |
| 2017/0049653 A1 | 2/2017 | Lim et al. | |
| 2018/0177536 A1 * | 6/2018 | Divincenzo | A61B 17/7091 |
| 2018/0368893 A1 * | 12/2018 | DiVincenzo | A61B 17/1604 |

FOREIGN PATENT DOCUMENTS

| | | | |
|---|---|---|---|
| CN | 103860247 A | 6/2014 | |
| CN | 104736078 A | 6/2015 | |
| CN | 105682583 A | 6/2016 | |
| EP | 1946711 A1 | 7/2008 | |
| EP | 2896378 A1 | 7/2015 | |
| JP | 2013540453 A | 11/2013 | |
| WO | 2007058673 A1 | 5/2007 | |
| WO | 2014062694 A1 | 4/2014 | |
| WO | 2017031225 A1 | 2/2017 | |

OTHER PUBLICATIONS

Japan Patent Office, Notice of Reasons for Rejection, Patent Application No. 2020-501807, dated Dec. 24, 2021.
China National Intellectual Property Administration (CNIPA), Notice on the First Office Action, Application/Patent No. 201880045652.3, dated Nov. 1, 2022.

* cited by examiner

SPINAL IMPLANT SYSTEM AND METHOD

CROSS REFERENCE TO RELATED APPLICATIONS

This application is a continuation of U.S. patent application Ser. No. 15/661,962, filed on Jul. 27, 2017, which is hereby expressly incorporated herein by reference, in its entirety.

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. Surgical treatment may employ surgical instruments and implants that are manipulated for engagement with vertebrae to position and align one or more vertebrae. This disclosure describes an improvement over these prior technologies.

SUMMARY

In one embodiment, a surgical instrument is provided. The surgical instrument comprises a first member including a drive engageable with a first mating surface of a bone fastener. A second member is rotatable relative to the first member and includes an element engageable with a second mating surface of the bone fastener. An actuator is connected with the second member and includes visual indicia of engagement of the element with the second mating surface. In some embodiments, systems, spinal implants and methods are disclosed.

In one embodiment, the surgical instrument includes an outer tubular sleeve extending between a proximal end and a distal end. The distal end including a drive engageable with a drive socket of a bone fastener shaft. An inner shaft is rotatable relative to the sleeve and includes a screw connectable with an inner threaded surface of a bone fastener receiver. A rotatable actuator is connected with the inner shaft and includes visual indicia of a non-locking configuration and a locking configuration with the inner threaded surface.

In one embodiment, a spinal implant system is provided. The spinal implant system comprises a surgical instrument including an outer tubular sleeve extending between a proximal end and a distal end including a drive engageable with a bone fastener shaft. An inner shaft is rotatable relative to the sleeve and includes a screw connectable with a threaded surface of a bone fastener receiver. The surgical instrument further includes a rotatable actuator connected with the inner shaft and includes visual indicia of a non-locking configuration and a locking configuration with the threaded surface. A guide member includes an inner surface that defines a cavity configured for disposal of the sleeve and an image guide is oriented relative to a sensor to communicate a signal representative of a position of the guide member.

BRIEF DESCRIPTION OF THE DRAWINGS

The present disclosure will become more readily apparent from the specific description accompanied by the following drawings, in which.

DETAILED DESCRIPTION

Figure 1:
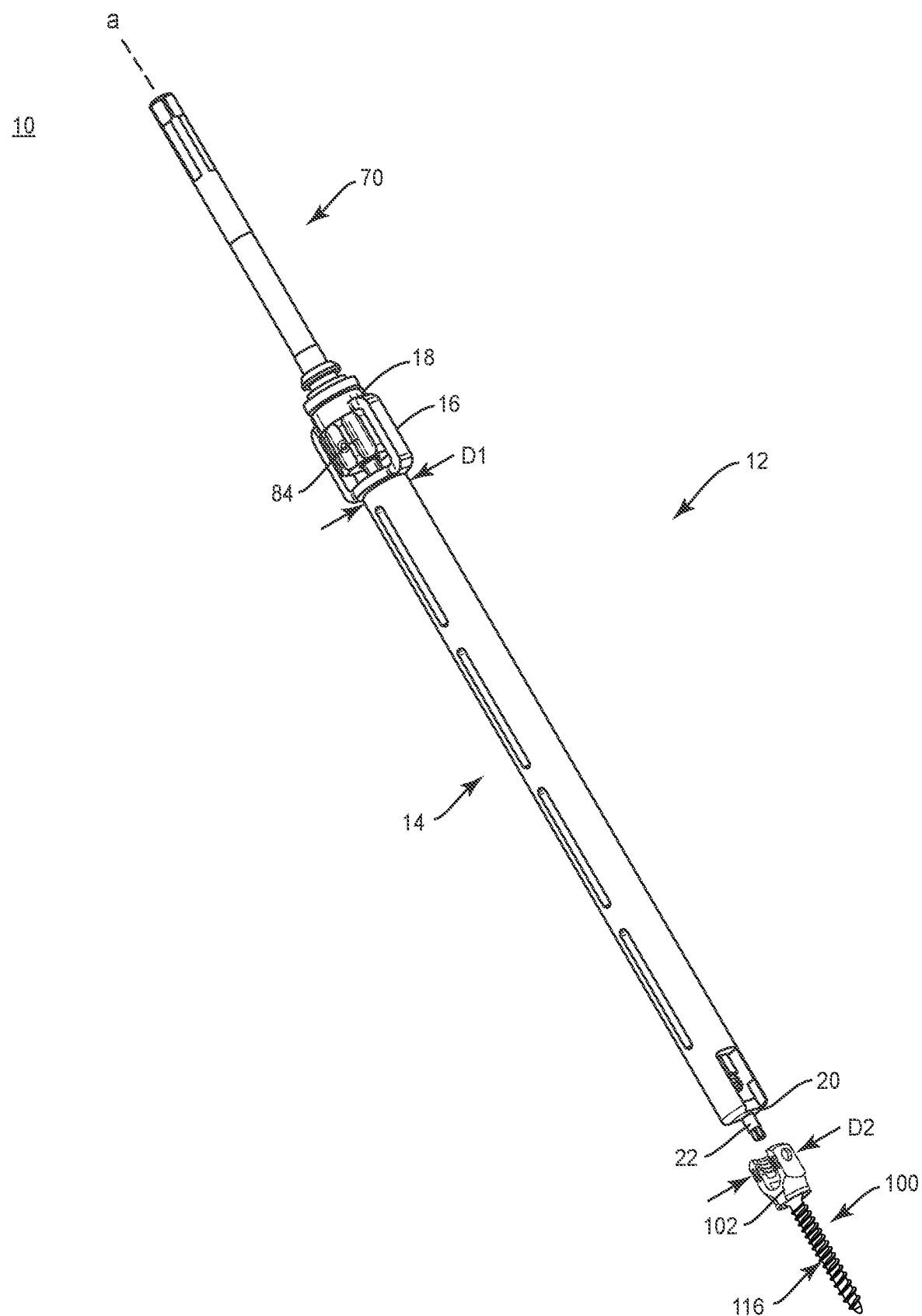
FIG. 1 is a perspective view of components of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a spinal implant system and a method for treating a spine. In some embodiments, the systems and methods of the present disclosure comprise medical devices including surgical instruments and implants that are employed with a surgical treatment, as described herein, for example, with a cervical, thoracic, lumbar and/or sacral region of a spine.

In some embodiments, the present surgical system comprises a surgical instrument that comprises a screw driver that can be employed with bone fasteners and one or more implant supports, such as, for example, an extender, for treating a spine. In some embodiments, the present surgical system includes a surgical instrument that can easily connect and disconnect from a bone fastener. In some embodiments, an extender can be connected in alignment with the surgical instrument to facilitate manipulation. In some embodiments, the present surgical system includes a surgical instrument that can be employed with an end effector of a robotic arm to facilitate implant with the robotic arm. In some embodiments, the surgical instrument is guided through the end effector for a guide-wireless screw insertion. In some embodiments, the surgical instrument comprises a robot screw driver employed with robotic and/or navigation guidance, which may include an image guide.

In some embodiments, the present surgical system comprises a surgical instrument that comprises a screw driver with a disengagement feature. In some embodiments, the present surgical system comprises a surgical instrument that comprises a screw driver with a disengagement feature for robotic guidance. In some embodiments, the screw driver includes a knob that serves as a visual indicator of whether or not the driver is fully disengaged from an implant. In some embodiments, the screw driver is employed with robotic guidance and has an inner shaft assembly that provides indicia of the driver being fully unthreaded from an implant. In some embodiments, the screw driver provides visual indicia that the screw driver is unthreaded from the implant in a minimally invasive surgical procedure. For example, the screw driver provides visual indicia whether the screw driver is or is not engaged.

In some embodiments, the present surgical system comprises a surgical instrument that comprises a driver having a torx tip configured for engagement with a bone fastener. In some embodiments, the driver includes a thumb wheel configured to actuate translation of the thumbwheel between a first, engaged positon and a second disengaged position. In some embodiments, in the engaged position, the torx tip is engaged with the bone fastener. In some embodiments, the thumb wheel is configured to indicate the position of the torx tip relative to the bone fastener. In some embodiments, the thumb wheel is configured to be pushed and rotated to engage the torx tip with the bone fastener. In some embodiments, the thumb wheel is disposed in the second positon and the driver is disengaged from the bone fastener. In some embodiments, the driver is configured for use with an open tulip bone fastener. In some embodiments, the driver includes an inner shaft configured for translation relative to an outer sleeve. In some embodiment, the inner shaft includes a threaded end configured for engagement with the bone fastener. In some embodiments, the position of the thumb wheel provides a visual indicator of engagement and disengagement of the inner shaft with the bone fastener. In some embodiments, the visual indicator facilitates removal of the driver in minimally invasive surgical procedures.

In some embodiments, the present surgical system comprises a method of assembly for a surgical instrument that comprises a driver. In some embodiments, the method includes the step of inserting a thumb wheel and a screw with an outer sleeve. In some embodiments, the method includes the step of translating an inner shaft into the outer sleeve and through the thumb wheel and the screw. In some embodiments, the method includes the step of engaging a pin with the thumb wheel and the inner shaft to fix the thumb wheel with the inner shaft. In some embodiments, the method includes the step of engaging a pin with the screw and the inner shaft to fix the screw with the inner shaft. In some embodiments, the pins are connected by laser welding. In some embodiments, the method includes the step connecting a quick connect shaft with the outer sleeve. In some embodiments, the quick connect shaft is welded to the outer sleeve.

In some embodiments, the present surgical system includes a screw driver having an outer shaft and a drive tip that engages a bone fastener. In some embodiments, the outer shaft and the drive tip are of one piece construction. In some embodiments, the one piece construction allows tolerances to be controlled tightly for improved accuracy of trajectory during implant insertion. In some embodiments, the drive tip includes a Torx configuration. In some embodiments, the present surgical system includes a screw driver having an internal retention mechanism. In some embodiments, the retention mechanism is fixed with a receiver of a bone fastener to resist and/or prevent disengagement of the retention mechanism from the receiver, for example, due to connection or friction with the end effector or tissue.

In some embodiments, the present surgical system includes a screw driver for use with robotic surgery. In some embodiments, the screw driver can be employed with fixed-axis screws (FAS), uni-axial screws (UAS), sagittal adjusting screws (SAS), transverse sagittal adjusting screws (TSAS) and multi-axial screws (MAS) screws, and allows the screws to be driven through a robotic end effector. In some embodiments, the screw driver includes a one piece outer sleeve having a tip. In some embodiments, the screw driver includes an internal retaining device that prevents accidental disengagement and/or unthreading.

In some embodiments, the present surgical system includes a screw driver including an outer shaft or sleeve having an outside diameter that is slightly larger than a screw spin diameter of a bone screw. This configuration allows the bone screw and the screw driver to pass through an end effector. In some embodiments, the screw driver includes a thumb wheel that is connected to a retention screw that threads into the bone screw.

In some embodiments, the present surgical system includes a screw driver that includes a quick connect shaft, an inner shaft, a thumb wheel, an outer driver shaft and a retention screw. In some embodiments, the screw driver includes cleaning slots for flushing and/or cleaning. In some embodiments, the surgical system is employed with a method for treating spinal trauma and/or deformity disorders with a minimally invasive surgical technique.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-12, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a fully open surgical procedure, a minimally invasive procedure including percutaneous techniques, and mini-open surgical techniques to deliver and introduce instrumentation and/or a spinal implant, such as, for example, a bone fastener, at a surgical site of a patient, which includes, for example, a spine. In some embodiments, the spinal implant can include one or more components of one or more spinal constructs, such as, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

Spinal implant system 10 includes a surgical instrument, such as, for example, a driver 12. Driver 12 can be employed with an end effector 200 (FIG. 10) of a robotic arm R (FIG. 12) to facilitate implant with robotic arm R. Driver 12 is guided through end effector 200 for guide-wireless insertion of a spinal implant, such as, for example, a bone fastener 100, as described herein.

Driver 12 includes a member, such as, for example, an outer tubular sleeve 14. Outer sleeve 14 extends between a proximal end 18 and a distal end 20. Outer sleeve 14 defines a longitudinal axis a. In some embodiments, outer sleeve 14 may have various configurations including, for example, round, oval, polygonal, irregular, consistent, variable, uniform and non-uniform. Outer sleeve 14 includes a diameter D1. In some embodiments, diameter D1 is slightly larger than a screw spin diameter D2 of bone fastener 100. This configuration allows bone fastener 100 and driver 12 to pass through end effector 200 of the robotic arm, as described herein.

Figure 6:
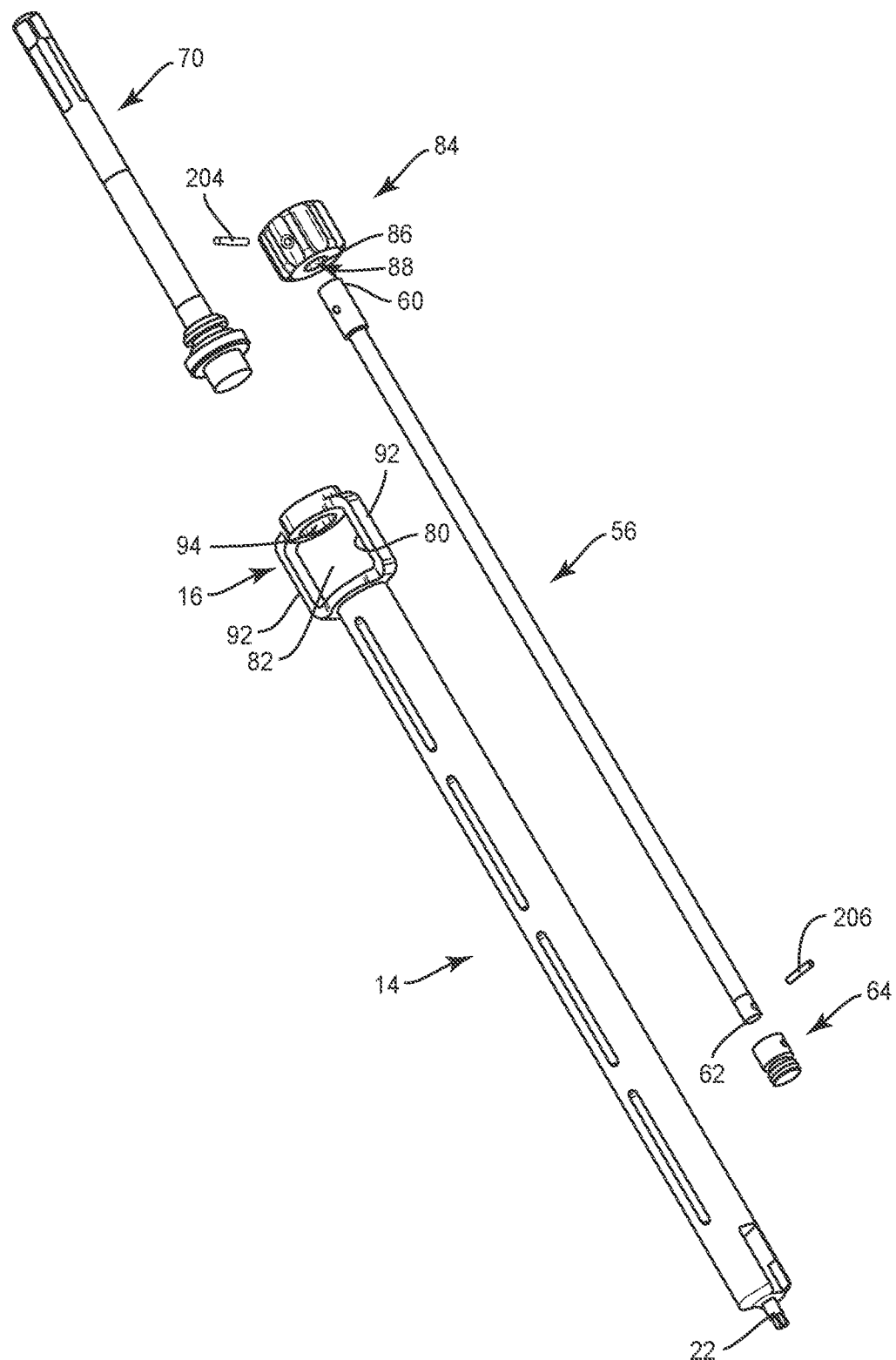
FIG. 6 is a perspective view of components of one embodiment of a surgical system in accordance with the principles of the present disclosure with parts separated.
Figure 7:
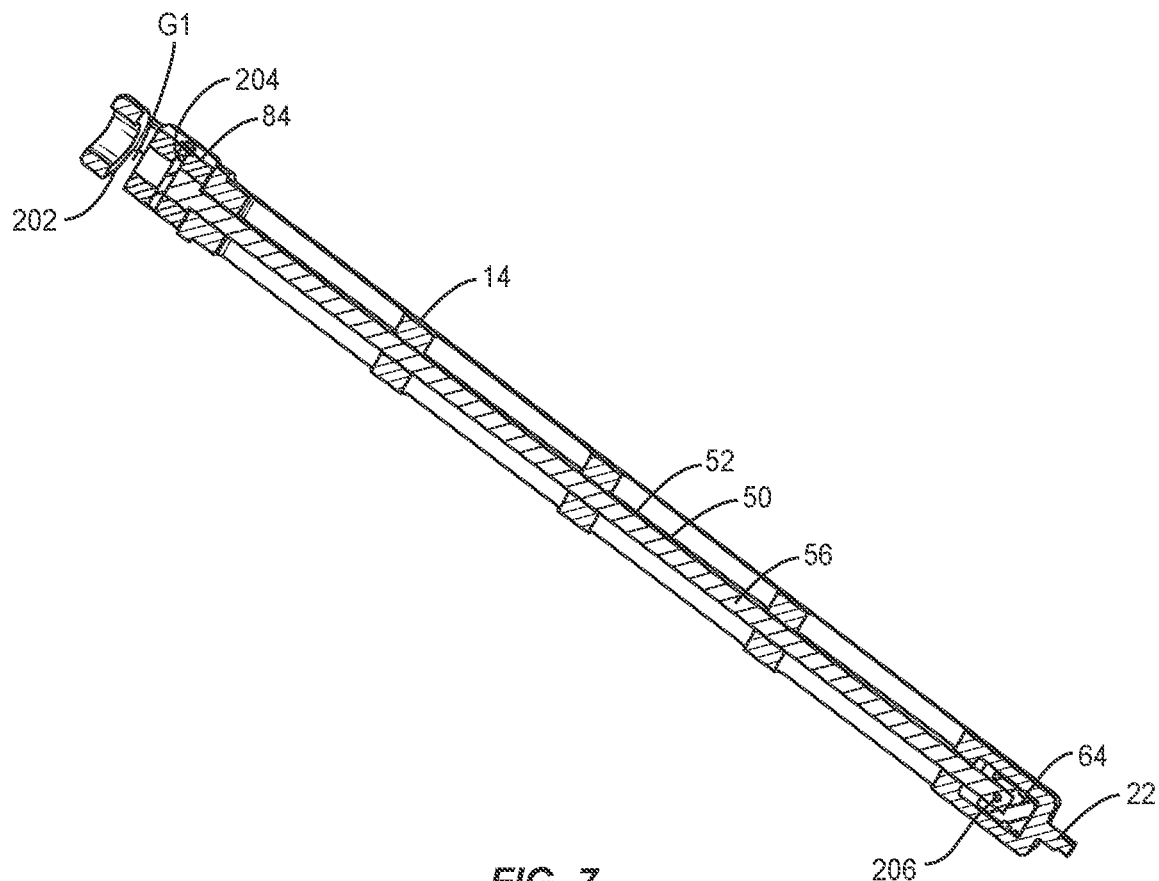
FIG. 7 is a cross section view of components of one embodiment of a surgical system in accordance with the principles of the present disclosure.
Figure 8:
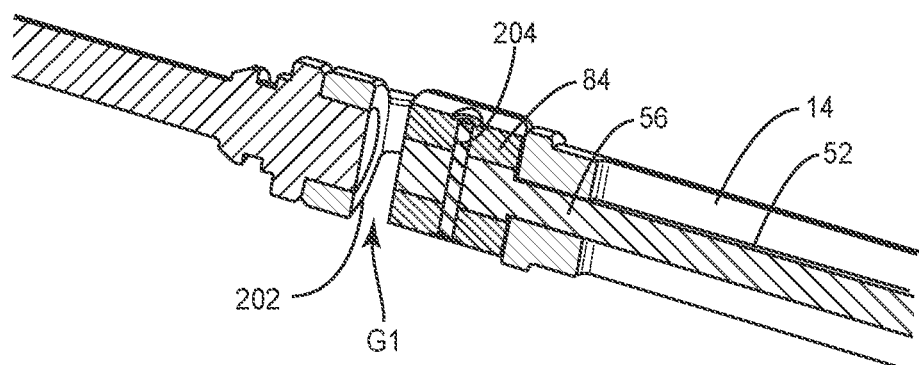
FIG. 8 is a break away view of the components shown in FIG. 7.
Figure 9:
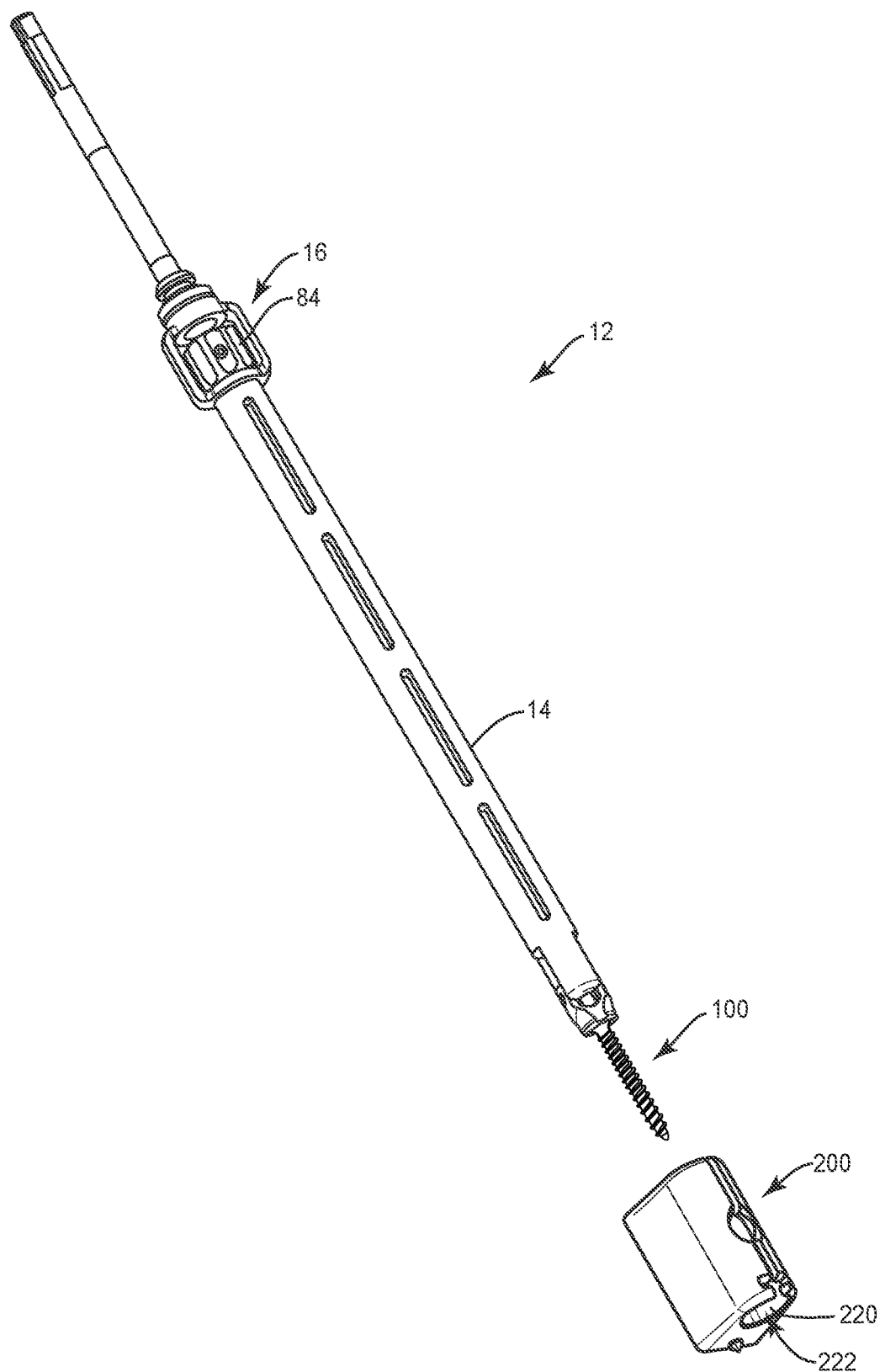
FIG. 9 is a perspective view of components of one embodiment of a surgical system in accordance with the principles of the present disclosure.
Figure 10:
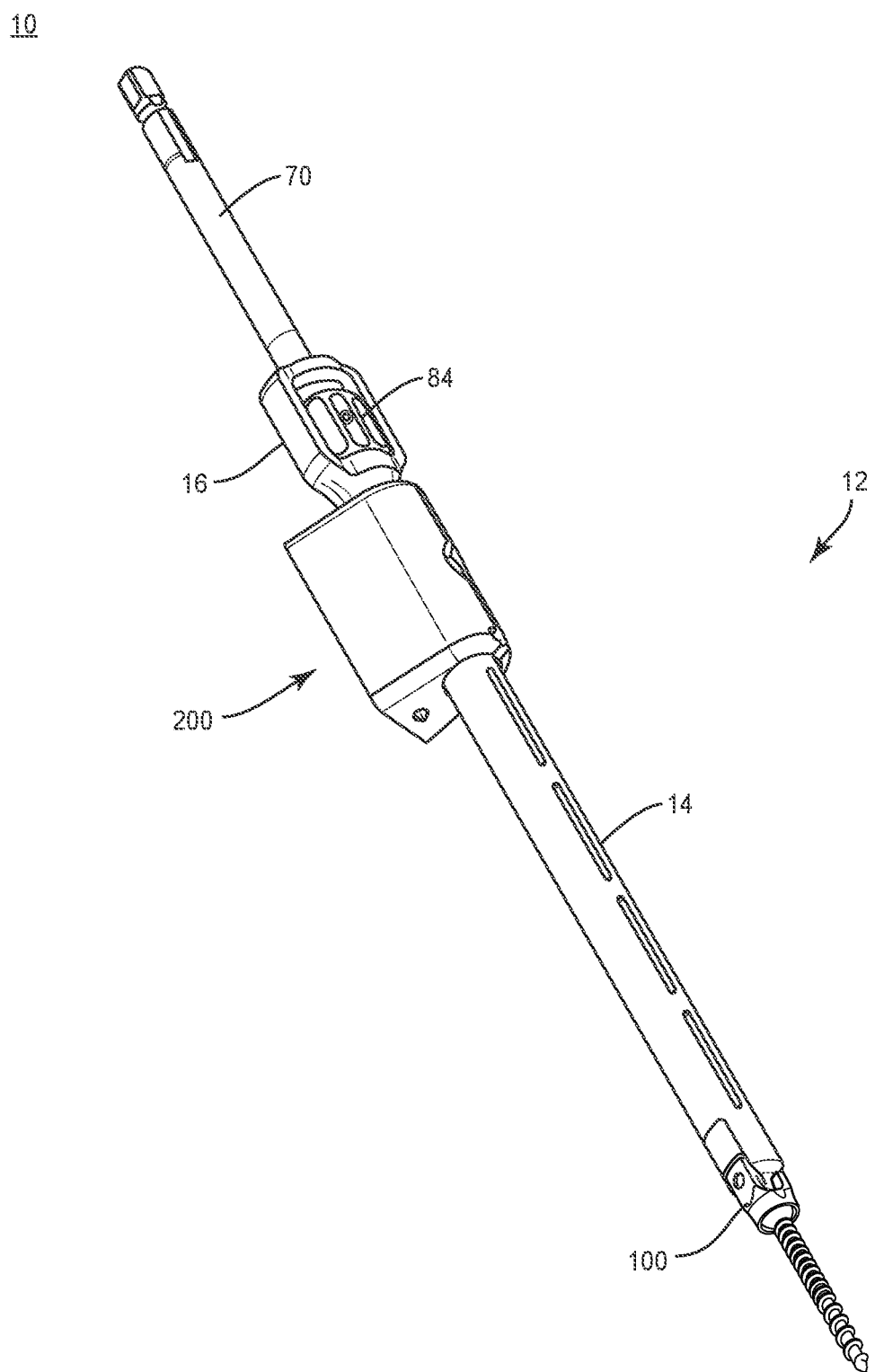
FIG. 10 is a perspective view of components one embodiment of a surgical system in accordance with the principles of the present disclosure.

Outer sleeve 14 includes a surface 50 that defines a channel 52. Channel 52 is configured for disposal of a member, such as, for example, an inner shaft 56 and an engagement element, such as, for example, a screw 64, as described herein. Outer sleeve 14 includes a collar body 16 having a surface 80. Surface 80 defines a cavity 82. Body 16 includes bifurcated arms 92 disposed about cavity 82 to facilitate disposal and access to an actuator, such as, for example, a thumb wheel 84 therein. Body 16 includes opening 94 disposed at end 18. Opening 94 is in communication with cavity 82 and in alignment with channel 52 to facilitate insertion of inner shaft 56 into end 18, through wheel 84 and into channel 52 for assembly, as described herein. Wheel 84 is configured to actuate rotation of inner shaft 56 and screw 64, as described herein. Wheel 84 includes a surface 86 that defines a cavity 88. Cavity 88 is configured for disposal of a correspondingly shaped portion of inner shaft 56, as shown in FIGS. 6-8.

Inner shaft 56 extends between an end 60 and an end 62. End 60 is engageable with wheel 84 for rotation of inner shaft 56 and screw 64, as described herein. In some embodiments, inner shaft 56 is fixed with wheel 84 by a pin 204, as shown in FIG. 6. Pin 204 is configured to fix wheel 84 relative to inner shaft 56 to resist and/or prevent rotation of wheel 84 relative to inner shaft 56 to facilitate simultaneous rotation of wheel 84, inner shaft 56 and screw 64, as described herein. In some embodiments, surface 86 engages end 60 in an interference fit. In some embodiments, cavity 88 includes various configurations, such as, for example, hexalobe, cruciform, phillips, square, hexagonal, polygonal, star cross sectional configuration for a mating engagement with correspondingly shaped portion of inner shaft 56. In some embodiments, wheel 84 includes a surface 90 configured to facilitate gripping of wheel 84, such as, for example a knurled surface.

Screw 64 includes an inner surface 66. Surface 66 defines a cavity 68 configured for disposal of a correspondingly shaped portion of end 62 of inner shaft 56. In some embodiments, inner shaft 56 is fixed with screw 64 by a pin 206, as shown in FIG. 6. Pin 206 is configured to fix screw 64 relative to inner shaft 56 to resist and/or prevent rotation of screw 64 relative to inner shaft 56 to facilitate simultaneous rotation of wheel 84, inner shaft 56 and screw 64, as described herein. In some embodiments, surface 66 engages inner shaft 56 in an interference fit. In some embodiments, cavity 68 includes various configurations, such as, for example, hexalobe, cruciform, phillips, square, hexagonal, polygonal, star cross sectional configuration for a mating engagement with a correspondingly shaped end 62. Screw 64 includes an outer surface having a thread form 89. Thread form 89 is configured for engagement with a mating surface, such as, for example, thread forms of arms 104, 106 of bone fastener 100 to pull and or draw bone fastener 100 into engagement with driver 12, as described herein.

Figure 2:
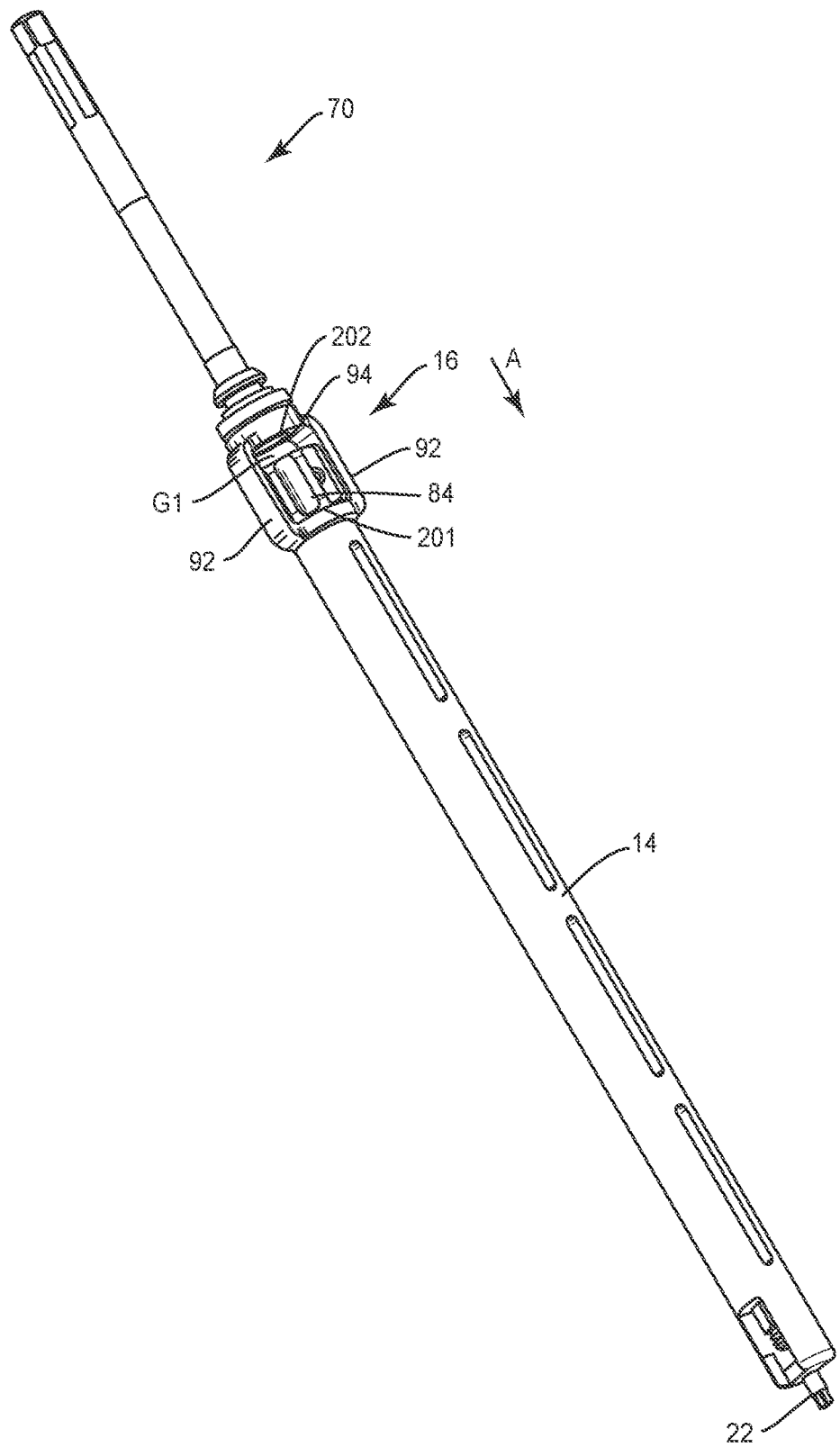
FIG. 2 is a perspective view of components of one embodiment of a surgical system in accordance with the principles of the present disclosure.
Figure 3:
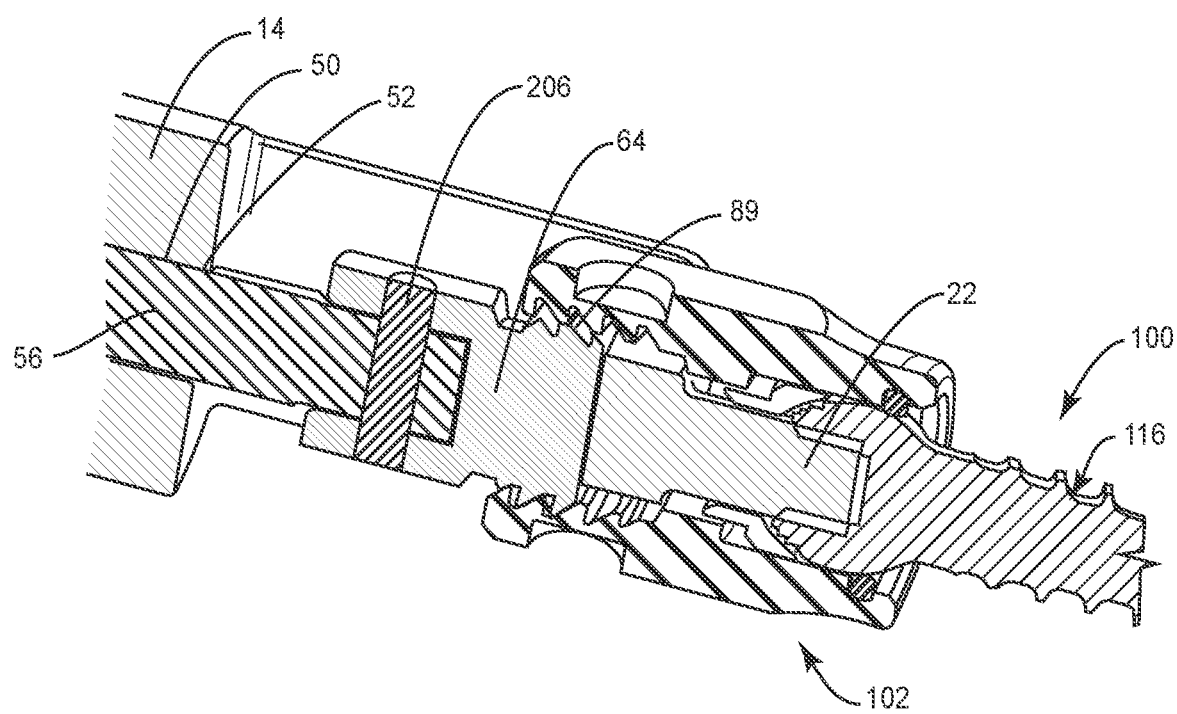
FIG. 3 is a break away cross section view of components of one embodiment of a surgical system in accordance with the principles of the present disclosure.
Figure 4:
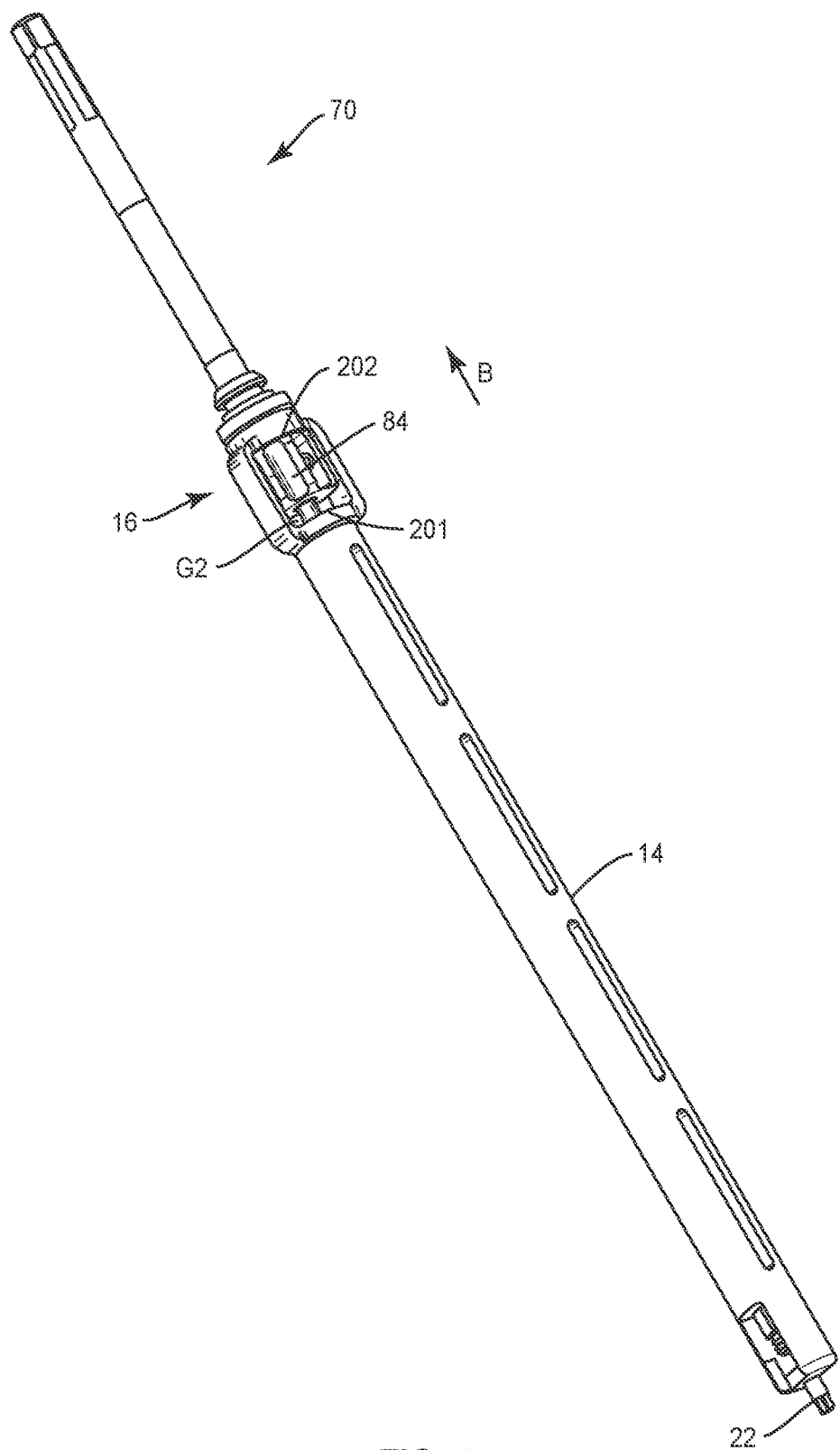
FIG. 4 is a perspective view of components of one embodiment of a surgical system in accordance with the principles of the present disclosure.
Figure 5:
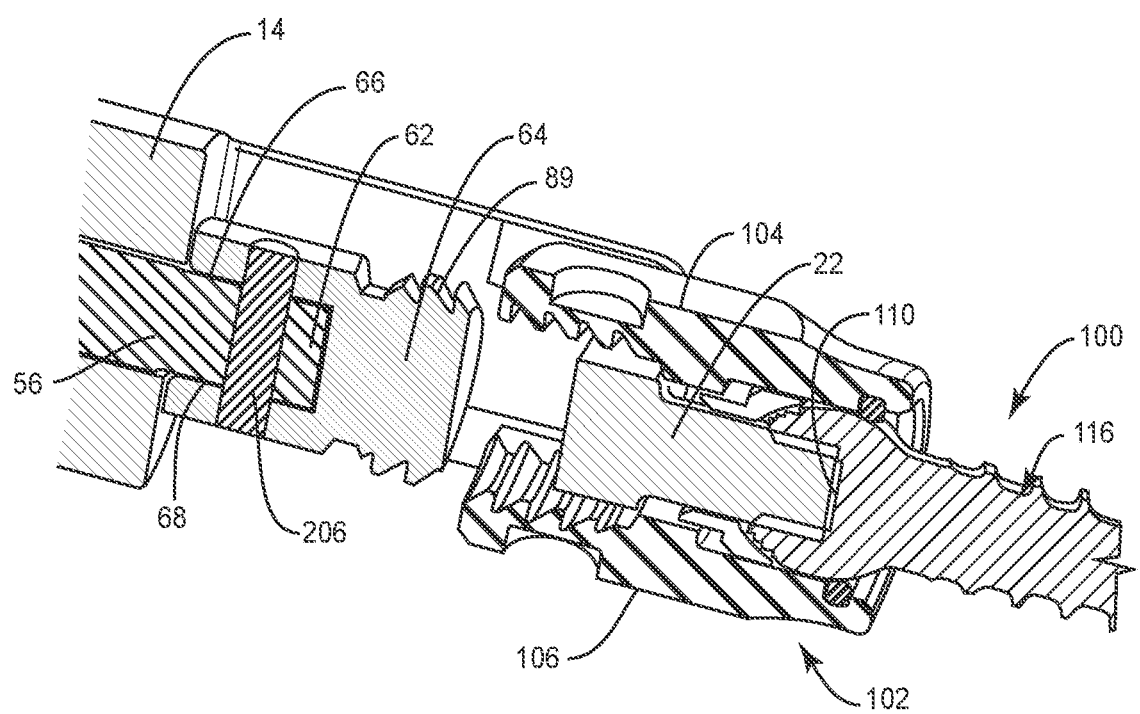
FIG. 5 is a break away cross section view of components of one embodiment of a surgical system in accordance with the principles of the present disclosure.

Wheel 84 is translatable within cavity 82 causing simultaneous axial movement of inner shaft 56 and screw 64 relative to outer sleeve 14. In some embodiments, body 16 includes ends 201, 202. Ends 201, 202 define a range of axial translation of wheel 84 relative to outer sleeve 14. Wheel 84 is moveable relative to outer sleeve 14 between a proximal position and a distal position. In the proximal position, wheel 84 provides visual indicia of a non-locking configuration of screw 64 relative to bone fastener 100, as shown in FIGS. 4 and 5. In the distal position, wheel 84 provides visual indicia of a locking configuration of screw 64 relative to bone fastener 100, as shown in FIGS. 2 and 3.

Wheel 84 provides visual indicia displaying the locking and/or non-locking configuration of screw 64 by a position of wheel 84 relative to outer sleeve 14. For example, wheel 84 translates, in a direction shown by arrow A in FIG. 2, such that a gap G1 is viewable. Gap G1 is disposed between wheel 84 and end 202. Gap G1 is viewable to indicate that screw 64 is disposed in the locking configuration relative to bone fastener 100. Wheel 84 translates, in a direction shown by arrow B in FIG. 4, closing gap G1 such that a gap G2 is viewable. Gap G2 is disposed between wheel 84 and end 201. Gap G2 is viewable to indicate that screw 64 is disposed in the non-locking configuration relative to bone fastener 100. Translation of wheel 84 and the visual indicia indicating the disengaged, non-locking configuration of screw 64 relative to bone fastener 100 facilitates removal of driver 12 in minimally invasive surgical procedures.

In some embodiments, the indicia of a non-locking and/or a locking configuration may include alternative visual indicia, tactile indicia, audible indicia, one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals. In some embodiments, the indicia includes a notch, slot, bead, detent, bump, print, label, score, color coding and/or cavity disposed on wheel 84. In some embodiments, the indicia may be attachable with or adhered to wheel 84.

Figure 11:
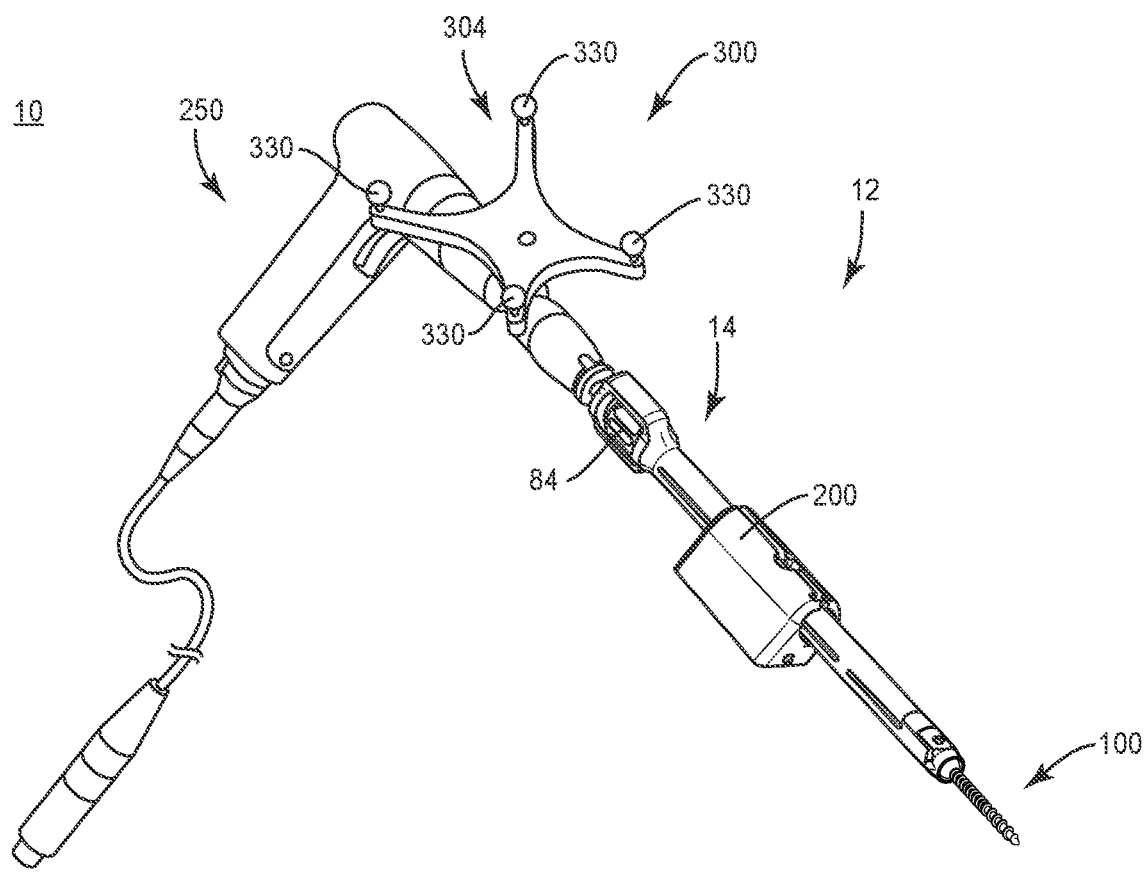
FIG. 11 is a perspective view of components one embodiment of a surgical system in accordance with the principles of the present disclosure.

Screw 64 is inserted laterally into channel 52. Wheel 84 is inserted laterally into cavity 82. With wheel 84 and screw 64 provisionally assembled with outer sleeve 14, inner shaft 56 is inserted from end 18, through opening 94, through cavity 88 and into channel 52 such that end 62 engages and passes through screw 64. Screw 64 is disposed with inner shaft 56 and wheel 84 is disposed with collar body 16, within channel 52, for assembly of the components of driver 12. As shaft 70 is inserted and attached with end 18 to assemble and retain inner shaft 56, wheel 84, and screw 64 within channel 52 in a relatively movable configuration with outer sleeve 14, as described herein. In some embodiments, shaft 70 is attached with end 18 such that inner shaft 56, wheel 84, screw 64 simultaneously slide, translate, rotate and/or float within channel 52. Inner shaft 56 retains screw 64 and wheel 84 with sleeve 14. In some embodiments, shaft 70 is welded with outer sleeve 14. In some embodiments, shaft 70 is configured to facilitate connection of driver 12 with a surgical instrument, such as, for example, an actuator/drill 250, as shown in FIG. 11. In some embodiments, shaft 70 includes quick connect surfaces or keyed geometry, such as, for example, triangle, hex, square or hexalobe to facilitate connection with actuator 250.

End 20 of outer sleeve 14 includes a distal tip, such as, for example, drive 22, as shown in FIG. 4. Drive 22 is integrally connected or monolithically formed with outer sleeve 14. This configuration facilitates control of tolerances to optimize accuracy of the connection of outer sleeve 14 with bone fastener 100. Drive 22 is engageable with a spinal implant, such as, for example, bone fastener 100. For example, drive 22 fits with and is engageable with a mating surface, such as, for example, a socket 110 of bone fastener 100. Rotation of outer sleeve 14 simultaneously rotates drive 22 to drive, torque, insert or otherwise connect bone fastener 100 with tissue, as described herein. In some embodiments, drive 22 includes a hexalobe geometry for a mating engagement with a correspondingly shaped socket 110. In some embodiments, drive 22 can alternatively include a cruciform, phillips, square, hexagonal, polygonal, star cross sectional configuration for disposal of a correspondingly shaped socket 110.

Bone fastener 100 includes receiver 102. Receiver 102 extends along axis a when connected with outer sleeve 14. Receiver 102 includes a pair of spaced apart arms 104, 106 that define an implant cavity configured for disposal of a component of a spinal construct, such as, for example, a spinal rod (not shown). Receiver 102 includes socket 110 configured for engagement with drive 22, as described herein. Receiver 102 includes an inner surface having a thread form located adjacent arm 104 and a thread form located adjacent arm 106. The thread forms of arms 104, 106 are configured for engagement with thread form 89 to retain bone fastener 100 with driver 12, as described herein. Bone fastener 100 includes a threaded shaft 116. Shaft 116 is configured to penetrate tissue, such as, for example, bone.

In use, bone fastener 100 is connected with driver 12, as described herein, and drive 22 is oriented for engagement with socket 110. Drive 22 is engaged with socket 110 and screw 64 is disposed with inner shaft 56 and assembled with outer sleeve 14 for axial translation relative to outer sleeve 14 and along inner shaft 56 between a non-locking configuration, as shown in FIGS. 4 and 5, and a locking configuration, as shown in FIGS. 2 and 3 with a spinal implant, such as, for example, bone fastener 100.

Wheel 84 is disposed in the proximal position and provides visual indicia, including gap G2, of the non-locking configuration of screw 64 relative to bone fastener 100, as shown in FIG. 4. Drive 22 is engaged with socket 110 such that bone fastener 100 is connected with outer sleeve 14, and thread form 89 is aligned with the thread forms of arms 104, 106 for engagement therebetween to retain bone fastener 100 with driver 12, as shown in FIG. 5. Wheel 84 is manipulated for rotation such that inner shaft 56 rotates screw 64 relative to and independent of outer sleeve 14. Thread form 89 engages the thread forms of arms 104, 106 and screw 64 axially translates into receiver 102 and relative to inner shaft 56. The threaded engagement of screw 64 and receiver 102 pulls and/or draws bone fastener 100 into the locking configuration with driver 12 for releasable fixation therebetween, as shown in FIG. 3. Wheel 84 is disposed in the distal position and provides visual indicia, including gap G1, of the locking configuration of screw 64 relative to bone fastener 100, as shown in FIG. 2.

Drive 22 is connected with outer sleeve 14, as described herein, and outer sleeve 14 is rotated to drive, torque, insert or otherwise connect bone fastener 100 with adjacent tissue. Screw 64 remains releasably fixed with receiver 102, independent of outer sleeve 14 rotation and/or engagement or friction with components of spinal implant system 10 as described herein, to resist and/or prevent disengagement or unthreading of screw 64 from receiver 102. In some embodiments, wheel 84 is manipulated for rotation such that screw 64 rotates relative to outer sleeve 14, and thread form 89 disengages the thread forms of arms 104, 106. Screw 64 axially translates from receiver 102 to unthread driver 12 from receiver 102 such that wheel 84 is disposed in the proximal position and provides visual indicia, including gap G2, of the non-locking configuration of screw 64 relative to bone fastener 100, as shown in FIG. 4.

Figure 12:
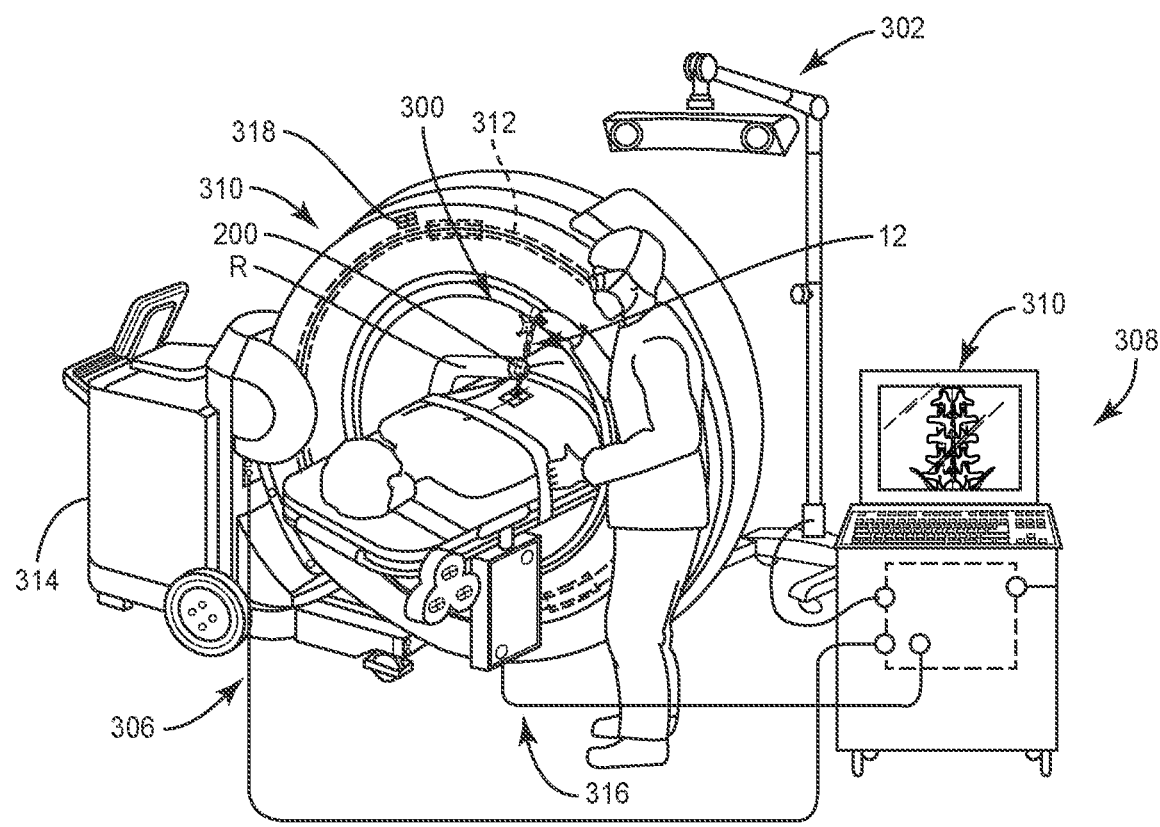
FIG. 12 is a perspective view of components of one embodiment of a surgical system in accordance with the principles of the present disclosure.

In some embodiments, driver 12 includes a navigation component 300, as shown in FIGS. 11 and 12. Driver 12 is configured for disposal adjacent a surgical site such that navigation component 300 is oriented relative to a sensor array 302 to facilitate communication between navigation component 300 and sensor array 302 during a surgical procedure, as described herein. Navigation component 300 is configured to generate a signal representative of a position of bone fastener 100 relative to driver 12 and/or tissue. In some embodiments, the image guide may include human readable visual indicia, human readable tactile indicia, human readable audible indicia, one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals. In some embodiments, navigation component 300 is connected with shaft 70 or outer sleeve 14 via an integral connection, friction fit, pressure fit, interlocking engagement, mating engagement, dovetail connection, clips, barbs, tongue in groove, threaded, magnetic, key/keyslot and/or drill chuck.

Navigation component 300 includes an emitter array 304. Emitter array 304 is configured for generating a signal to sensor array 302 of a surgical navigation system 306, as shown in FIG. 12 and described herein. In some embodiments, the signal generated by emitter array 304 represents a position of bone fastener 100 relative to driver 12 and relative to tissue, such as, for example, bone. In some embodiments, the signal generated by emitter array 304 represents a three dimensional position of bone fastener 100 relative to tissue.

In some embodiments, sensor array 302 receives signals from emitter array 304 to provide a three-dimensional spatial position and/or a trajectory of bone fastener 100 relative to driver 12 and/or tissue. Emitter array 304 communicates with a processor of computer 308 of navigation system 306 to generate data for display of an image on monitor 310, as described herein. In some embodiments, sensor array 302 receives signals from emitter array 304 to provide a visual representation of a position of bone fastener 100 relative to driver 12 and/or tissue. See, for example, similar surgical navigation components and their use as described in U.S. Pat. Nos. 6,021,343, 6,725,080, 6,796,988, the entire contents of each of these references being incorporated by reference herein.

Surgical navigation system 306 is configured for acquiring and displaying medical imaging, such as, for example, x-ray images appropriate for a given surgical procedure. In some embodiments, pre-acquired images of a patient are collected. In some embodiments, surgical navigation system 306 can include an O-arm® imaging device 310 sold by Medtronic Navigation, Inc. having a place of business in Louisville, Colo., USA. Imaging device 310 may have a generally annular gantry housing that encloses an image capturing portion 312.

In some embodiments, navigation system 306 comprises an image capturing portion 314 that may include an x-ray source or emission portion and an x-ray receiving or image receiving portion located generally or as practically possible 180 degrees from each other and mounted on a rotor (not shown) relative to a track of image capturing portion 314. Image capturing portion 314 can be operable to rotate 360 degrees during image acquisition. Image capturing portion 314 may rotate around a central point or axis, allowing image data of the patient to be acquired from multiple directions or in multiple planes. Surgical navigation system 306 can include those disclosed in U.S. Pat. Nos. 8,842,893; 7,188,998; 7,108,421; 7,106,825; 7,001,045; and 6,940,941; the entire contents of each of these references being incorporated by reference herein.

In some embodiments, surgical navigation system 306 can include C-arm fluoroscopic imaging systems, which can generate three-dimensional views of a patient. The position of image capturing portion 314 can be precisely known relative to any other portion of an imaging device of navigation system 306. In some embodiments, a precise knowledge of the position of image capturing portion 314 can be used in conjunction with a tracking system 316 to determine the position of image capturing portion 314 and the image data relative to the patient.

Tracking system 316 can include various portions that are associated or included with surgical navigation system 306. In some embodiments, tracking system 316 can also include a plurality of types of tracking systems, such as, for example, an optical tracking system that includes an optical localizer, such as, for example, sensor array 302 and/or an EM tracking system that can include an EM localizer. Various tracking devices can be tracked with tracking system 316 and the information can be used by surgical navigation system 306 to allow for a display of a position of an item, such as, for example, a patient tracking device, an imaging device tracking device 318, and an instrument tracking device, such as, for example, emitter array 304, to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, 5,592,939, the entire contents of each of these references being incorporated by reference herein.

Fluoroscopic images taken are transmitted a computer 314 where they may be forwarded to computer 308. Image transfer may be performed over a standard video connection or a digital link including wired and wireless. Computer 308 provides the ability to display, via monitor 310, as well as save, digitally manipulate, or print a hard copy of the received images. In some embodiments, images may also be displayed to the surgeon through a heads-up display.

In some embodiments, surgical navigation system 306 provides for real-time tracking of the position of bone fastener 100 relative to driver 12 and/or tissue can be tracked. Sensor array 302 is located in such a manner to provide a clear line of sight with emitter array 304, as described herein. In some embodiments, fiducial markers 330 of emitter array 304 communicate with sensor array 302 via infrared technology. Sensor array 302 is coupled to computer 308, which may be programmed with software modules that analyze signals transmitted by sensor array 302 to determine the position of each object in a detector space.

Driver 12 is configured for use with a guide member, such as, for example, an end effector 200 of a robotic arm R. End effector 200 includes a surface 220 that defines a cavity, such as, for example, a channel 222. Channel 222 is configured for passage of bone fastener 100 and disposal of driver 12. Robotic arm R includes position sensors (not shown), similar to those referenced herein, which measure, sample, capture and/or identify positional data points of end effector 200 in three dimensional space for a guide-wireless insertion of bone fasteners 100 with selected vertebral levels. In some embodiments, the position sensors of robotic arm R are employed in connection with surgical navigation system 306 to measure, sample, capture and/or identify positional data points of end effector 200 in connection with surgical treatment, as described herein. The position sensors are mounted with robotic arm R and calibrated to measure positional data points of end effector 200 in three dimensional space, which are communicated to computer 308.

In assembly, operation and use, spinal implant system 10, similar to the systems and methods described herein, is employed with a surgical procedure, such as, for example, a treatment of an applicable condition or injury of an affected section of a spinal column and adjacent areas within a body. In some embodiments, one or all of the components of spinal implant system 10 can be delivered or utilized as a pre-assembled device or can be assembled in situ. Spinal implant system 10 may be completely or partially revised, removed or replaced.

In use, to treat vertebrae (not shown), a medical practitioner obtains access to a surgical site in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby the vertebrae is accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal implant system 10. A preparation instrument (not shown) can be employed to prepare tissue surfaces of the vertebrae as well as for aspiration and irrigation of a surgical region.

Pilot holes (not shown) are made in selected levels of vertebrae for receiving bone fasteners 100. Wheel 84 is disposed in the proximal position and provides visual indicia, including gap G2, of the non-locking configuration of screw 64 relative to bone fastener 100, as shown in FIG. 4. Bone fastener 100 is connected with driver 12, as described herein. Wheel 84 is rotated such that threaded engagement of screw 64 and receiver 102 pulls and/or draws bone fastener 100 into the locking configuration with driver 12 for releasable fixation therebetween, as shown in FIG. 3. Wheel 84 is disposed in the distal position and provides visual indicia, including gap G1, of the locking configuration of screw 64 relative to bone fastener 100, as shown in FIG. 2.

Driver 12, connected with bone fastener 100, is oriented for disposal with end effector 200 of robotic arm R, as described herein. The assembly of driver 12/bone fastener 100 is disposed with channel 220 for implantation of one or more bone fasteners 100 with vertebrae employing robotic arm R and/or surgical navigation system 306, as described herein. Actuator 250 is connected with shaft 70 and drive 22 engages bone fastener 100, as described herein, and outer sleeve 14 is rotated to drive, torque, insert or otherwise connect bone fastener 100 with adjacent tissue. Screw 64 remains releasably fixed with receiver 102, independent of outer sleeve 14 rotation and/or engagement or friction with end effector 200 to resist and/or prevent disengagement or unthreading of screw 64 from receiver 102. In some embodiments, driver 12 is manipulated to deliver one or more bone fasteners 100 to a surgical site including vertebrae.

Sensor array 302 receives signals from navigation component 300 to provide a three-dimensional spatial position and/or a trajectory of the assembly of driver 12/bone fastener 100, which may be disposed with end effector 200, relative to vertebrae and/or components of spinal implant system 10 for display on monitor 310. Wheel 84 is manipulated for rotation such that screw 64 rotates relative to outer sleeve 14, and thread form 89 disengages the thread forms of arms 104, 106. Screw 64 axially translates from receiver 102 to unthread driver 12 from receiver 102 such that wheel 84 is disposed in the proximal position and provides visual indicia, including gap G2, of the non-locking configuration of screw 64 relative to bone fastener 100, as shown in FIG. 4.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiomarkers may be included for identification under x-ray, fluoroscopy, CT or other imaging techniques. In some embodiments, spinal implant system 10 may include one or a plurality of spinal rods, plates, connectors and/or bone fasteners for use with a single vertebral level or a plurality of vertebral levels.

In some embodiments, one or more bone fasteners, as described herein, may be engaged with tissue in various orientations, such as, for example, series, parallel, offset, staggered and/or alternate vertebral levels. In some embodiments, the bone fasteners may comprise multi-axial screws, sagittal adjusting screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:
1. A surgical instrument comprising:
a first member including a drive engageable with a first mating surface of a bone fastener; and
a second member including a screw engageable with a second mating surface of the bone fastener, the screw being fixed to a distal end of the second member by a pin, the screw having an outer thread surface connectable with the second mating surface, the first member defining an inner cavity, the second member being rotatably disposed within the inner cavity.

2. The surgical instrument recited in claim 1, wherein the screw has a maximum diameter, the maximum diameter of the screw being greater than a maximum diameter of the drive.

3. The surgical instrument recited in claim 1, wherein the first member includes a tubular wall extending along a longitudinal axis between opposite first and second end surfaces, the drive extending outwardly from the second end surface such that the drive is coaxial with the longitudinal axis.

4. The surgical instrument recited in claim 3, wherein the second end surface extends perpendicular to the longitudinal axis.

5. The surgical instrument recited in claim 1, wherein the first member includes a tubular wall extending along a longitudinal axis between opposite first and second end surfaces, the drive being spaced apart from the screw by the second end surface, the drive and the screw being coaxial with the longitudinal axis.

6. The surgical instrument recited in claim 5, wherein the second end surface extends perpendicular to the longitudinal axis.

7. The surgical instrument recited in claim 1, wherein the first member includes a tubular wall extending along a longitudinal axis between opposite first and second end surfaces, the drive extending outwardly from the second end surface such that the drive permanently fixed to the second end surface, the second end surface extending perpendicular to the longitudinal axis.

8. The surgical instrument recited in claim 1, wherein the first member includes a tubular wall extending along a longitudinal axis between opposite first and second ends, the second end including a window, the screw being visible through the window to confirm engagement of the outer thread surface with the second mating surface.

9. The surgical instrument recited in claim 8, wherein the first end includes a collar body, the collar body comprising bifurcated arms, the arms defining a cavity therebetween, the surgical instrument comprising a thumbwheel positioned in the cavity, the thumbwheel being configured to rotate the second member relative to the first member about the longitudinal axis.

10. The surgical instrument recited in claim 1, wherein the first member includes a tubular wall extending along a longitudinal axis between opposite first and second ends, the first end including a collar body, the collar body comprising bifurcated arms, the arms defining a cavity therebetween, the surgical instrument comprising a thumbwheel positioned in the cavity, the thumbwheel being configured to rotate the second member relative to the first member about the longitudinal axis.

11. The surgical instrument recited in claim 1, wherein the first member includes a tubular wall extending along a longitudinal axis between opposite first and second ends, the first end including a collar body, the collar body comprising first and second arms, the first arm being connected to the second arm by a ring, the ring comprising an opening, the opening being coaxial with the longitudinal axis, the surgical instrument comprising a shaft extending through the opening such that the shaft is fixed relative to the first member.

12. The surgical instrument recited in claim 11, wherein a distal end of the shaft extends through the opening and an opposite proximal end of the shaft comprises a polygonal cross-sectional configuration, the proximal end being configured for engagement with a drill, the proximal end having a maximum diameter, the maximum diameter of the proximal end being less than a maximum diameter of the distal end.

13. The surgical instrument recited in claim 1, wherein the drive comprises a distal tip of the first member and the first mating surface includes a drive socket of a bone fastener shaft.

14. The surgical instrument recited in claim 1, further comprising a thumbwheel coupled to the first end, the thumbwheel being configured to rotate the second member relative to the first member about the longitudinal axis.

15. The surgical instrument recited in claim 14, wherein the thumbwheel is coupled to the first end by a pin and the first member is monolithic, the instrument consisting of the members, the pins and the thumbwheel.

16. A surgical system comprising:
a bone fastener including a screw and a receiver, the screw being rotatable relative to the receiver, the screw comprising a first mating surface, the receiver comprising a second mating surface; and
a surgical instrument comprising a first member including a drive, the drive being engageable with the first mating surface, the surgical instrument comprising a second member, the second member including a screw engageable with the second mating surface, the screw being fixed to a distal end of the second member by a pin, the screw having an outer thread surface connectable with the second mating surface, the first member defining an inner cavity, the second member being rotatably disposed within the inner cavity.

17. The surgical system recited in claim 16, wherein the screw has a maximum diameter, the maximum diameter of the screw being greater than a maximum diameter of the drive.

18. The surgical system recited in claim 16, wherein the first member includes a tubular wall extending along a longitudinal axis between opposite first and second end surfaces, the drive extending outwardly from the second end surface such that the drive and the screw are coaxial with the longitudinal axis, the screw being spaced apart from the drive by the second end surface, the second end surface extending perpendicular to the longitudinal axis.

19. A surgical system comprising:
a bone fastener including a screw and a receiver, the screw being rotatable relative to the receiver, the screw comprising a socket, the receiver comprising a female thread form; and
a surgical instrument comprising a first member including a drive, the drive being configured for disposal in the socket, the surgical instrument comprising a second member, the second member including a screw, the screw being fixed to a distal end of the second member by a pin, the screw comprising a male thread form engageable with the female thread form, the first member defining an inner cavity, the second member being rotatably disposed within the inner cavity.

20. The surgical system recited in claim 19, wherein the screw has a maximum diameter, the maximum diameter of the screw being greater than a maximum diameter of the drive.

* * * * *